US009069963B2

(12) United States Patent
Barnes, II

(10) Patent No.: US 9,069,963 B2
(45) Date of Patent: Jun. 30, 2015

(54) STATISTICAL INSPECTION SYSTEMS AND METHODS FOR COMPONENTS AND COMPONENT RELATIONSHIPS

(75) Inventor: Richard Lee Barnes, II, Arlington, VA (US)

(73) Assignee: Raytheon BBN Technologies Corp., Cambridge, MA (US)

( * ) Notice: Subject to any disclaimer, the term of this patent is extended or adjusted under 35 U.S.C. 154(b) by 79 days.

(21) Appl. No.: 13/542,198

(22) Filed: Jul. 5, 2012

(65) Prior Publication Data

US 2014/0012847 A1  Jan. 9, 2014

(51) Int. Cl.
*G06F 17/30* (2006.01)
*G06F 21/56* (2013.01)
*G06F 9/44* (2006.01)
*G06F 19/22* (2011.01)

(52) U.S. Cl.
CPC .............. *G06F 21/562* (2013.01); *G06F 8/75* (2013.01); *G06F 19/22* (2013.01)

(58) Field of Classification Search
CPC ........................... G06F 11/079; G06F 11/1482
USPC .......... 707/737, 797–798, 802–803; 717/120, 717/105, 154, 141, 143
See application file for complete search history.

(56) References Cited

U.S. PATENT DOCUMENTS

| 841,829 | A | * | 1/1907 | Nicci | 264/108 |
| 5,440,742 | A | * | 8/1995 | Schwanke | 717/120 |
| 5,778,361 | A | * | 7/1998 | Nanjo et al. | 1/1 |
| 2004/0093331 | A1 | * | 5/2004 | Garner et al. | 707/3 |
| 2007/0240221 | A1 | * | 10/2007 | Tuvell et al. | 726/24 |
| 2008/0276217 | A1 | * | 11/2008 | Nagaoka | 717/105 |
| 2010/0185686 | A1 | * | 7/2010 | Weigert et al. | 707/803 |
| 2010/0332583 | A1 | * | 12/2010 | Szabo | 709/202 |
| 2012/0072988 | A1 | * | 3/2012 | Agrawal | 726/24 |
| 2014/0012847 | A1 | * | 1/2014 | Barnes, II | 707/737 |

OTHER PUBLICATIONS

Bretto, A., "Hypergraph lossless image compression", International Conference on Information Technology: Coding and Computing, 2005. ITCC 2005., 46-50.
Chen, Chia-Ping, et al., "Image set compression through minimal-cost prediction structure", 2004 International Conference on Image Processing, 2004. ICIP '04., 1289-1292.

(Continued)

*Primary Examiner* — Hung T Vy
(74) *Attorney, Agent, or Firm* — Schwegman Lundberg & Woessner, P.A.

(57) ABSTRACT

Embodiments of an inspection system and method for a collection of information objects, for example, a collection of executable software applications may be inspected for computer viruses, or a collection of genomes may be inspected for common or unique gene sequences. Information objects may contain identified sequences of instructions, each of which may be labeled with a symbol. In the software context, programming languages may include symbols that indicate functionality. In some embodiments, an inspection of the statistical properties of the information objects and their included symbols may allow for the symbols (and thus instruction sequences) to be grouped into logical components. In some embodiments, objects that include individual logical components may be grouped together. These groupings and their dependencies may be used to determine the structure of each object by detailing its constituent components, how they relate or depend on one another, and how the information object may function.

21 Claims, 9 Drawing Sheets

(56) References Cited

OTHER PUBLICATIONS

Feige, Uriel, "A threshold of In n for approximating set cover", J. ACM, 45(4), (1998), 634-652.

Keller, R. K, et al., "Pattern-based reverse-engineering of design components", Proceedings of the 1999 International Conference on Software Engineering, 1999., 226-235.

Mitchell, Brian S, et al., "Comparing the Decompositions Produced by Software Clustering Algorithms using Similarity Measurements", ICSM 2001, 10 pgs.

Mitchell, Brian S, "On the automatic modularization of software systems using the Bunch tool", IEEE Transactions on Software Engineering, 32(3), (2006), 193-208.

Muller, H., "A reverse-engineering approach to subsystem structure identification", J. Softw. Maint: Res. Pract., 5, (1993), 181-204.

Niere, Jorg, et al., "Towards Pattern-Based Design Recovery", Proceedings of the 24th International Conference on Software Engineering, (2002), 338-348.

Zerbino, Daniel R, et al., "Velvet: Algorithms for de novo short read assembly using de Bruijn graphs", Genome Res.,18(5), (May 2008), 821-829.

\* cited by examiner

1. Extract from the object a unique name and a list of symbols in the object.

2. Initialize a set of new components T as the empty set.

3. Construction of a component for symbols unique to the object:{
Construct a new component including the symbols in the object and the object's name.
Remove from the new component any symbols contained in libraries already in the graph.
If the component contains no symbols after the prior step, discard it.
If the component contains symbols, add it to the set of new components T.}

4. For each component C in the graph, perform the following:
{
4.1. If the component C contains no symbols from the new object, do nothing.

4.2. Otherwise, if all of the symbols in the component C are contained in the object, update the component and patch edges: {
Add the object's name to the component's list of objects.
Remove all inbound edges to the component C.
Initialize a set A as the set of components with outbound edges to C.
Initialize a set B as the set of components with inbound edges from C.
For each component X in A and Y in B, patch around C: {
    Determine whether there is a path from X to Y in the graph (excluding C).
    If there is no path, add an edge from X to Y. }
Add the component C to the set of new components T. }

4.3. Otherwise, split the component, according to the following: {
Compute the set of symbols that are common to both the component and the object.
Remove the common symbols from the component.
Create a new component with the following contents: {
    Symbols: The common symbols.
    Objects: The object names from the old component, plus the new object's name.}
Add the new component to the list of new components.
Add the new component to the graph.
Add to the graph a directed edge from the new component to the old component.
Add the new component to the set of new components T. }
}
    TO FIG. 7B

*FIG. 7A*

FROM FIG. 7A

6. Synthesize edges among new components in T according to the following:
{
Initialize a set E of new edges to the empty set.
For each pair of new components A, B in T, add to E a directed edge from A to B if the set of objects in B is a subset of the set of objects in A.
Remove redundant edges from E, according to the following: {
  Initialize a set N to the set of components in T with outbound but no inbound edges.
    While the set N is non-empty, select a component X: {
      Compute the set P of components that have an inbound edge from X.
      Compute the set Q of components that have an inbound edge from any component in P.
      Remove X from N.
      Remove from E any edges from X to components in Q.
      Add the components in P to the set N.}
  }
Remove from the graph any existing edges between components in T.
Add to the graph the edges in E.
}

*FIG. 7B*

A set of Objects with no unique Symbols

STATISTICAL INSPECTION SYSTEMS AND METHODS FOR COMPONENTS AND COMPONENT RELATIONSHIPS

STATEMENT REGARDING FEDERALLY SPONSORED RESEARCH OR DEVELOPMENT

This invention was made with government support under award number H98230-09-C-0279 awarded by the National Security Agency. The government has certain rights in this invention.

TECHNICAL FIELD

Embodiments pertain to computer program inspection. Some embodiments relate to detecting genetic relationships. Some embodiments relate to statistical inspection and compression. Some embodiments relate to constructing hierarchical relationships between component groups based on identified dependencies between symbols in computer program objects.

BACKGROUND

The problem of separating an object into its constituent components, thereby allowing an analysis of the internal structure of the object based on those components, is a long-standing problem in reverse engineering complex systems. For example, in the software analysis field reverse engineering mechanisms typically examine individual objects in isolation, and base a decomposition of components on properties internal to the object. These techniques tend to be slow and inaccurate because they rely on detailed information about an object and on fuzzy, heuristic decisions.

An example of a method of performing a system reverse engineering process is described in U.S. Pat. No. 6,978,228. U.S. Pat. No. 5,675,711 provides an example of adaptive statistical regression and classification of data strings, with application to the generic detection of computer viruses.

Computer malware detection has typically been conducted with the use of programs that monitor files and application on individual computers. The detection methods often rely on large databases that contain signatures of previously identified computer viruses, worms, trojans, spyware, or other malicious computer programs. Malware scanning programs search individual files on individual computers searching for known signatures. While this pattern detection approach can be effective it requires frequent updates to the database of signatures to keep abreast of the most recent malware developments.

Interest by the reverse engineering and anti-malware communities in analysis of mobile applications has increased due to the widespread public adoption of mobile communication devices such as smart phones that include large amounts of personal data that may be subject to exploitation by malicious programs. There are also general needs for malware detection systems and methods that are suitable for screening applications before they are distributed to, or used with, mobile communication devices such as smart phones.

Genome analysis also presents the problem of breaking down objects into their constituent components. Sequences of DNA in a genome may include vast numbers of individual genes that may be challenging to recognize or identify. Additionally, even after a gene is identified, the function of an individual gene, or the interaction of multiple genes, may not be apparent without significant research into specific genes.

BRIEF DESCRIPTION OF THE FIGURES

Embodiments discussed in the present document are illustrated, by way of example, and not limitation, in the Figures of the accompanying drawings in which:

FIGS. 7A and 7B illustrate an example of a scheme for constructing a directed graph, in accordance with some embodiments.

DETAILED DESCRIPTION

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments. Embodiments set forth in the claims encompass all available equivalents of those claims.

Reverse engineering efforts have typically focused on performing analysis of individual applications. However, the emergence of modern software repositories (e.g., mobile app stores) has created large populations of applications that reside in a single location. These large populations of applications provide a pool that may serve as a basis for statistical component inspection and analysis of the individual applications based on common features and dependencies that emerge from the pool.

Systems and methods for inspecting a population of information objects, such as a collection of executable software applications or one or more genomes, for categorization and analysis. For example, information objects may contain identified sequences of instructions or chemical markers, each of which may be labeled with a symbol or recognized as a reoccurring pattern. In the software application context, some programming languages such as Objective-C®, Java®, and .NET® include symbol information in their resulting executable programs. Because application binary formats may include symbols for class names, these symbols may be used as a proxy for the constituent instruction sequences. For example, a mechanism for interrogating, identifying and analyzing structural properties of software applications may simplify the development of reverse engineering or anti-malware detection systems, or provide insights into the origin, authorship or functionality of one or more software applications when the source code for the application is unavailable.

Information objects may be identified by a name, an assigned identifier, a calculation that identifies the object uniquely, such as a hash of the object, or any other mechanism that allows one object to be distinguished from another object. Symbols may be identified by a name, an assigned symbol identifier, a calculation that identifies the symbol uniquely, such as a hash of the symbol, or any other mechanism that allows one symbol to be distinguished from another symbol, and similarly provides for an accurate determination of identity between two symbols in a comparison.

Figure 1B:
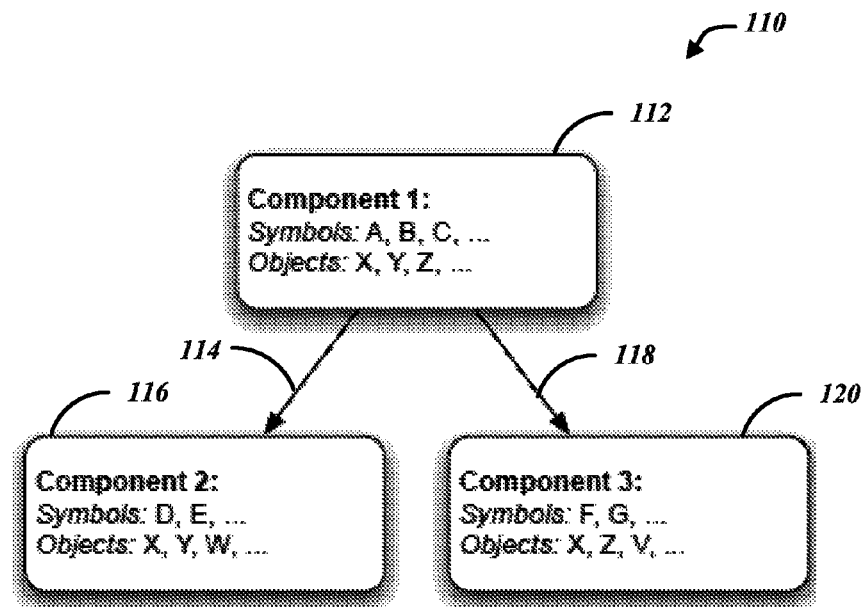
FIG. 1B illustrates an example directed graph of components from a population of symbols in objects, in accordance with some embodiments.
Figure 1A:
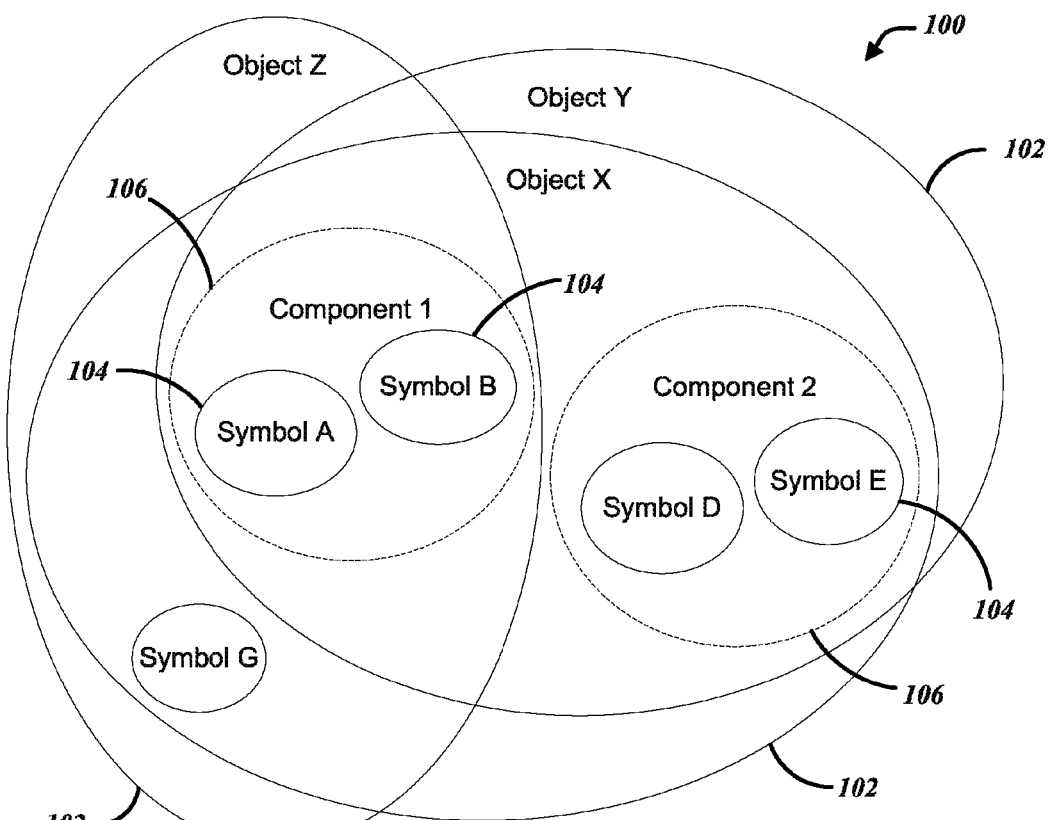
FIG. 1A illustrates an example group of objects that includes a population of symbols, in accordance with some embodiments.

FIG. 1A illustrates an example group 100 of information objects 102 that includes a population of symbols 104. In this example Object X and Object Y both include Symbols A, B, D and E, and Object X and Object Z both include Symbols A, B and G. Other symbols 104 may be included in one, some, or all of the information objects 102. An inspection of multiple information objects 102, and their embedded symbols 104, may allow the symbols 104 to be grouped into logical components 106 based on the inclusion of the embedded symbols 104 in one or more information objects 102, Because symbols 104 may represent corresponding instruction sequences or functionality it is possible to determine or infer which objects 102 may share instruction sequences, common program code, genetic markers, genes, DNA sequences or functionality. The statistical properties, relationships and dependencies of the symbols 104 and logical components 106 can be analyzed to provide data about the information objects 102, and to predict information object behavior or characteristics.

Information objects 102 that include each logical component 106 may also be grouped together based on their common components 106. These groupings and their relationships may be used to determine the structure of each object by detailing its constituent symbols or components and how they relate or depend on one another. For example, the decomposition of objects 102 into components 106 may be based on symbol information that can be very quickly extracted from the objects 102, and based on relationships and dependencies of components 106 in a population of objects.

In an example embodiment a group of objects 100 may be inspected by interrogating each of a plurality of objects 102 for one or more symbols 104 that are embedded in the objects 102. Any dependencies between the symbols 104 may be identified based on the presence of the symbols in at least two of the plurality of objects 102. A plurality of component groups that include objects 102 that share identical symbols 104 may be constructed. Additionally, hierarchical relationships between the plurality of component groups may be constructed based on, and to illustrate, the identified dependencies between the symbols in the plurality of objects.

FIG. 1B illustrates an example directed graph 110 of components from a population of symbols in objects, such as the example group of objects 100 depicted in FIG. 1A. The objects may include a collection of executable programs, such as some or all of the applications available from a mobile application store. The components may include libraries of symbols that are utilized by the executable programs. Alternatively, the objects may include a genome comprising a plurality of gene components, or a database design comprising a collection of data sets.

Directed graph 110 includes nodes that represent components (112, 116, 120) derived from a set of objects (X, Y, Z, etc.) and their included symbols (A, B, C, D, etc.). The components may be stored in an appropriate data structure that includes a component name or identifier, and fields for both symbol and object identifiers. Graph 110 may be constructed by analyzing a population of symbols contained in a group of objects.

For example, component node 112 in the graph 110 represents a first component that contains a list of symbols (A, B, C) and a list of information objects (X, Y, Z) that contain the symbol and therefore include the component. Symbols and objects may be grouped into a component if the symbols appear in exactly the same set of information objects. In other words, components may be constructed to list only those objects that include one or more identical symbols, which are also included in the component.

Generally, given two symbols C and D that are grouped into separate components (i.e., they are both not always present in every object), one can infer that symbol C depends on symbol D if the set of objects containing symbol C is a subset of the class containing D. That is, symbol C depends on symbol D if symbol D is always present when symbol C is present. Symbol C may be present in an object without symbol D.

Graph 110 includes a first directed edge 114 from component 112 to component 116, and a second directed edge 118 from component 112 to component 120 because the symbols in the component 116 and component 120 appear only when the symbols in component 112 are present. In other words, components 116 and 120 depend on component 112, As used herein, edges are described as being inbound, from the perspective of a dependent component, if the edge extends from an independent component to the dependent component. Similarly, from the perspective of an independent component, an outbound edge extends to a dependent component from the independent component. For example, edge 114 may be considered an outbound edge from the perspective of component 112 and an inbound edge from the perspective of component 116.

In the context of a computer application, a "save file" procedure identified as symbol C may be considered to depend on a "disk access" procedure identified as symbol D because every object (e.g., multiple computer applications) that includes the "save file" procedure (symbol C) also includes the "disk access" procedure (symbol D). Other applications may include the "disk access" procedure, but do not include the "save file" procedure. In this example, the "disk access" procedure (symbol D) is considered a more atomic operation than the "save file" procedure (symbol C).

Figure 2:
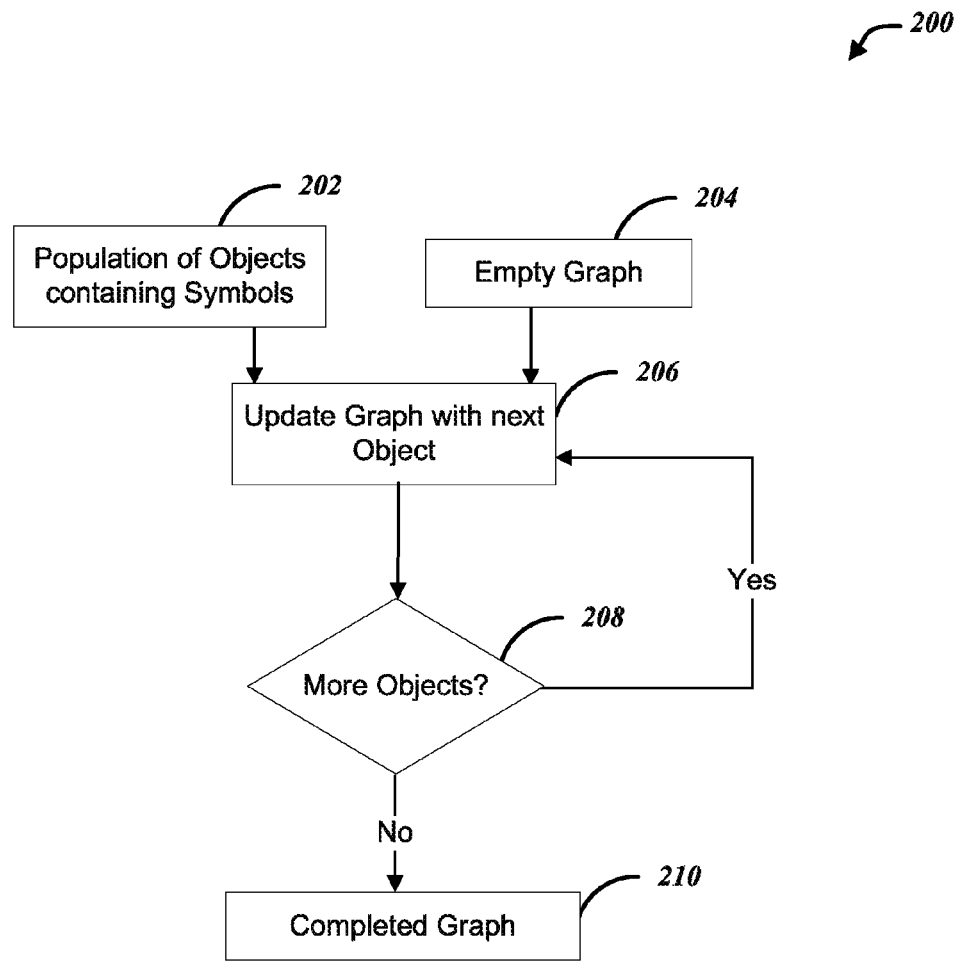
FIG. 2 illustrates a procedure for constructing a directed graph from a population of objects, in accordance with some embodiments.

FIG. 2 illustrates an example procedure 200 for constructing a directed graph from a population of objects. At 202, a population of objects is assembled for interrogation and analysis. The objects may include a collection of executable programs, such as some or all of the applications available from a mobile application store. Alternatively, the objects may include a genome comprising a plurality of genes, or a database design comprising a collection of data sets. Initially, at 204, the directed graph is empty, and has no components or edges (dependencies) between components.

At 206, the graph is updated to extract from an object a unique name or identifier, and a list of symbols included in the object. Any new components in the object are added to the graph, and any existing components or edges that are impacted by the addition of the object are updated. Each object in the population may be added to the graph individually by iterating through the population of objects. At 208, a check is made to determine if one or more additional objects are available to be added to the graph. At 210, the graph contains information about all components and object decompositions that may be gleaned from the population of objects. The graph may be incrementally updated as new objects are added to the population. Further details on object analysis and graph construction and updating are provided below with reference to exemplary FIGS. 3-7.

Figure 3:
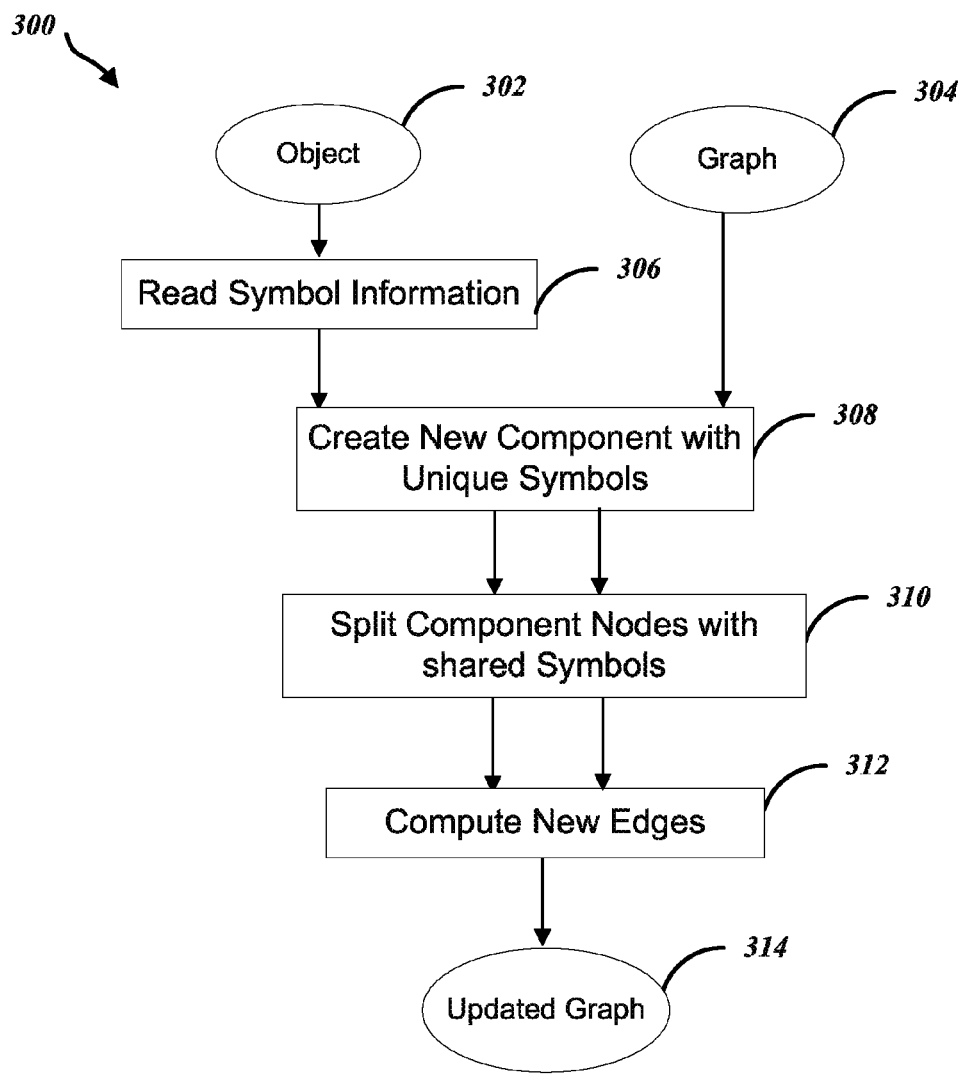
FIG. 3 illustrates a procedure for updating a graph with a new object, in accordance with some embodiments.

FIG. 3 illustrates a procedure 300 for updating a graph with a new object 302. If no objects have been previously added the set of components in the graph 304 is an empty set. At 306, upon receipt of a new object 302 all symbol information is read from the object 302 and compared to any existing symbols that may be present in the graph 304. For each object 302, after an initial object, the graph 304 may contain one or more existing components or edges connecting components. A set (T) to contain new components, which will later be added to the graph 304, is initialized as an empty set.

At 308, a new component that can contain symbols unique to object 302 is created. The new component can be constructed such that it initially includes all of the symbols read from the object 302, and the name object of object 302 or another unique object identifier. From this new component containing all symbols in an object 302, any symbols that are already contained in other components in the graph 304 are removed from the new component. If the new component contains no symbols after the removal of existing symbols already in the graph 304, then the new component may be discarded. If the new component is not empty after the removal of existing symbols the new component is added to a set of new components (T).

At 310, all components in the graph 304 are inspected to determine if any components should be split. If an individual component contains no symbols from the new object then no action is required for that individual component. If all of the symbols in an individual component are contained in the new object 302, then the individual component is updated and edges in the graph 304 are patched (e.g., new relationships between the components are computed).

New edges are computed to patch the edges of a component. The new object's name is added to the component's list of objects, all inbound edges to the individual component are removed, a first set (A) is initialized as the set of components with outbound edges to the individual component, and a second set (B) is initialized as the set of components with inbound edges from the individual component.

For each component X in first set A and component Y in second set B, patch around the individual component. A component may be patched around by determining whether there is a path from X to Y in the graph that excludes the individual component. If there is no path around the individual component, then an edge is added that extends from X to Y. Finally, the individual component is added to the set of new components (T).

Figure 4:
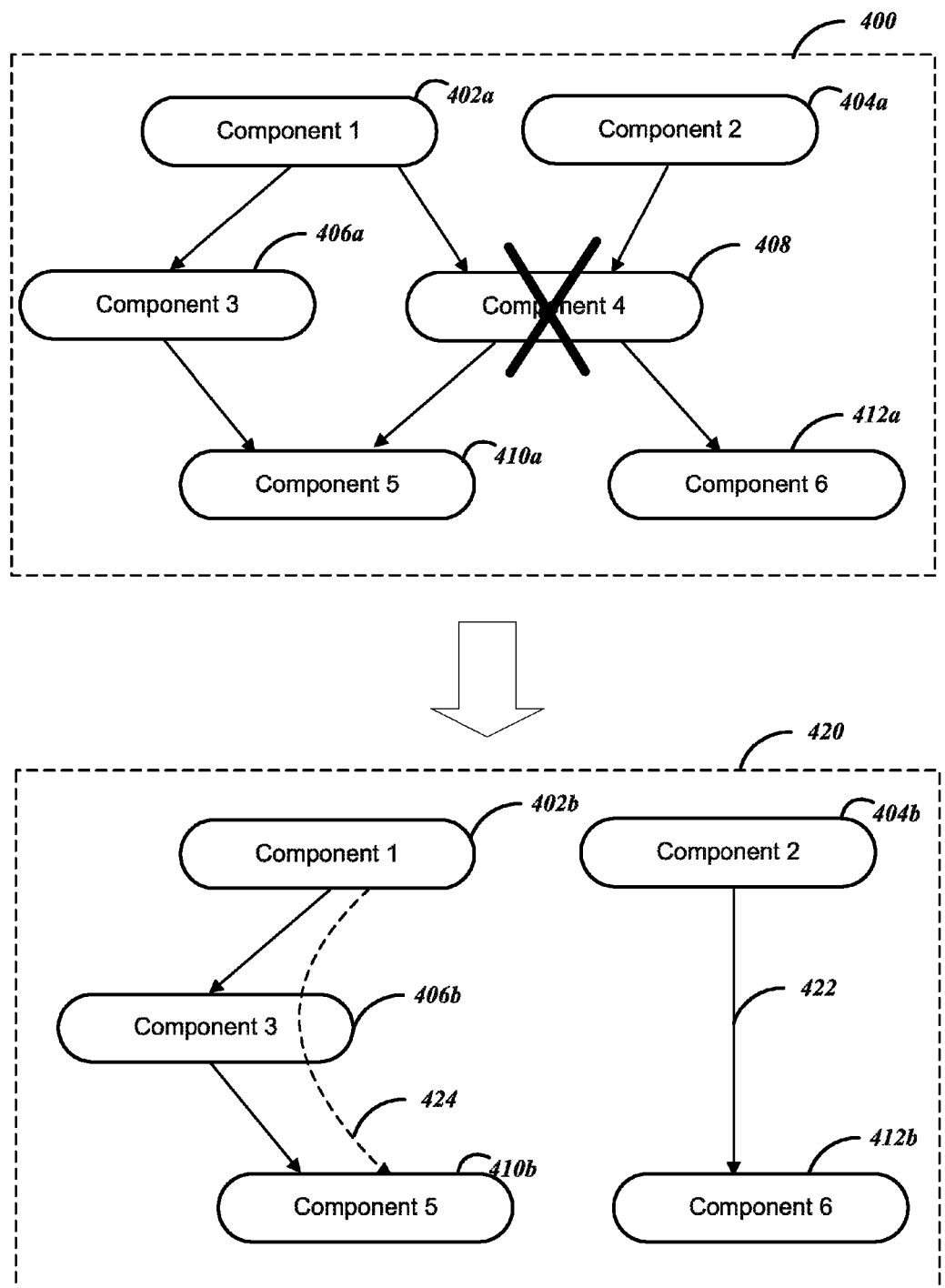
FIG. 4 illustrates an example of patching around a component, in accordance with some embodiments.

FIG. 4 illustrates an example of patching around a component. A pre-patch graph 404 may contain a plurality of component nodes (402, 404, 406, 408, 410, and 412). Component 402 and component 404 both include edges that are inbound to component 408. Component 410 and component 412 both include edges that are inbound from component 408. Component 408 provides a path from component 402 to component 410 that goes around component 408. A-post patch graph 420 includes a direct path 422 from component 404 to component 406, and an implicit path 424 from component 402 to component 410 that passes through component 406.

Figure 5:
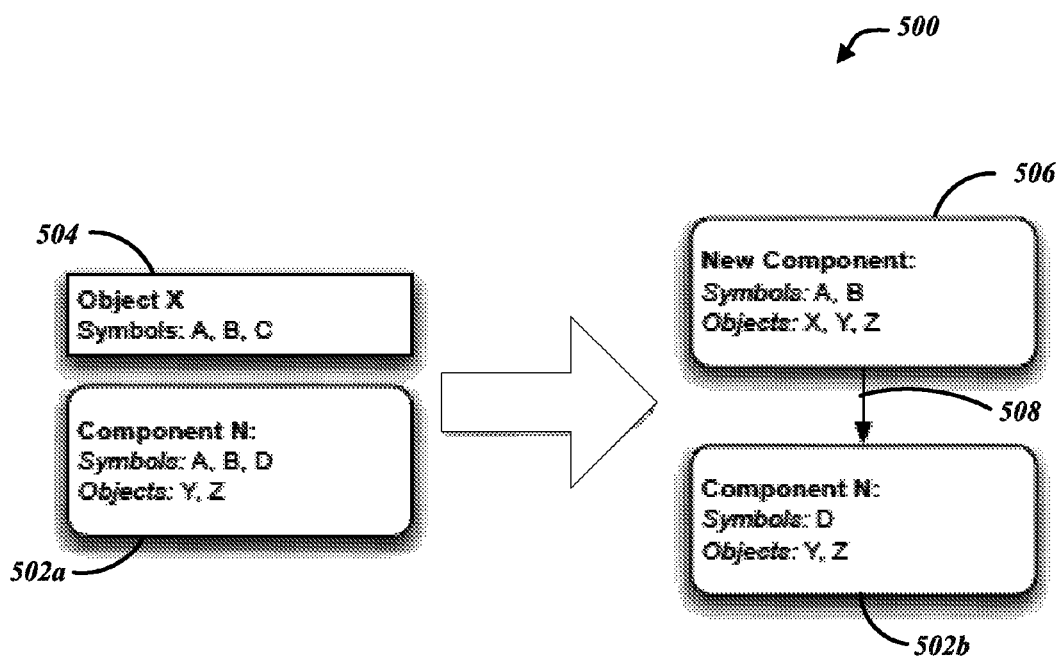
FIG. 5 illustrates a graph of splitting components to include information about a new object, in accordance with some embodiments.

If a component includes some, but not all, of the symbols that were added from the new object, then the component is split. An example of splitting a component is depicted in FIG. 5.

First, to split a component 502a, the set of symbols that are common to both the component 502a and the new object 504 are determined. In this example, component 502a and object (X) 504 both include symbol (A) and symbol (B). The symbols common to both are removed from the component 502a to create component 502b. Next, a new component 506 is created with contents that include both the common symbols and the objects from the original component 502a, and also the object name or identifier for the new object (X) 504.

The new component 506 is added to the list of new components, the new component is added to the graph, and a directed edge 508 is added from the new component 506 to the modified component 502b in the graph. Finally, the new component is added to the set of new components (T).

Referring again to FIG. 3, at 312, once all nodes in the graph have been inspected and split if necessary, edges among the set of new components in (T) are synthesized. For example, initially, a set (E) of new edges is initialized to the empty set. For each pair of new components (A, B) in the set of new components (T), a directed edge from A to B is added to set (E) if the set of objects in (B) is a subset of the set of objects in (A).

Figure 6:
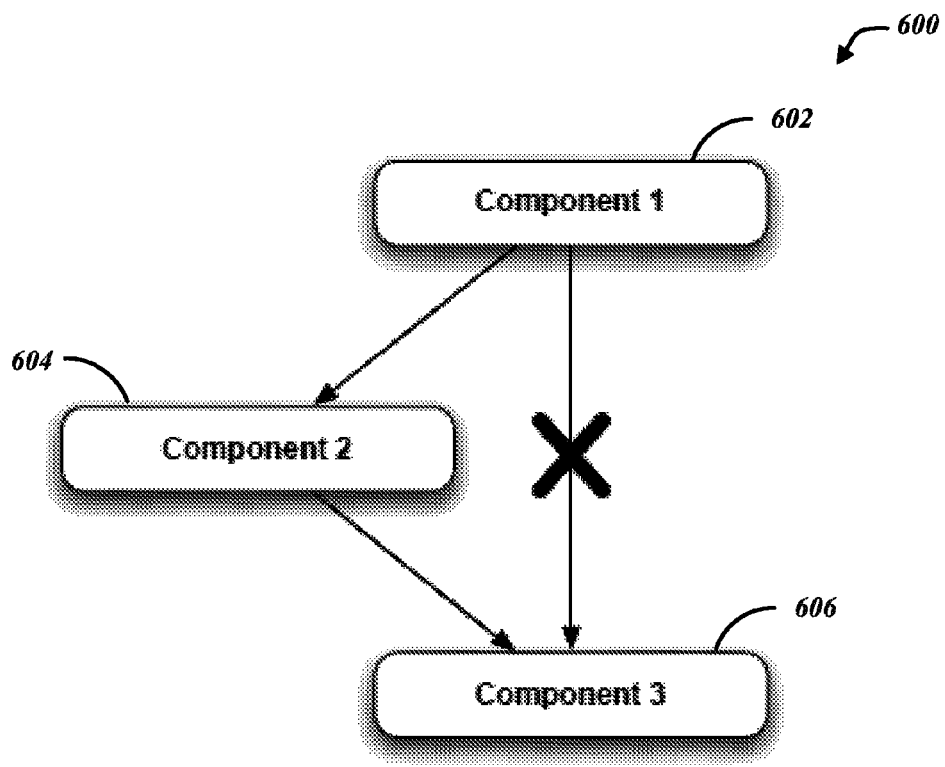
FIG. 6 illustrates an example of removing redundant edges between components, in accordance with some embodiments.

Once all of the dependencies between all of the components in the set of components (T) are added to set (E), the redundant edges are removed from E. FIG. 6 illustrates an example of removing redundant edges between components.

A set (N) is initialized to include the set of components in the set of new components (T) with outbound edges but no inbound edges. While the set (N) is not empty, select a component (X) and perform the following steps: compute the set (P) of components that have an inbound edge from component (X), compute the set (Q) of components that have an inbound edge from any component in (P), remove component (X) from set (N), remove from set (E) any edges from component (X) to components in set (Q), and add the components in set (P) to the set (N). Finally, when set N is empty, remove from the graph any existing edges between components in (T), and add the edges in (E) to the graph.

At 314, the graph contains information about the components and object decompositions that can be gleaned from the objects provided. An object can be decomposed into components by selecting the component nodes from the graph that contain the object's name. The graph may be computed incrementally as new objects are added to the population, and object decompositions can be updated accordingly.

FIGS. 7A and 7B illustrate an example of a pseudo code procedure for constructing a directed graph that may be utilized to interrogate each of a plurality of computer program objects stored for one or more symbols that are embedded in the objects; identify dependencies between the symbols based on the presence of the symbols in at least two of the plurality of computer program objects; construct a plurality of component groups that include computer program objects that share identical symbols; and construct hierarchical relationships between the plurality of component groups based on the identified dependencies between the symbols in the plurality of computer program objects.

Analysis of Genomes

The procedures discussed herein can also be applied to applications decomposing any of a variety of information objects that include instruction sequences. For example, genomes may be considered to be information objects, where each gene (e.g., DNA pairs) or gene sequence in the genome is an instruction or sequence that may be represented by a symbol and grouped into logical components. These procedures may be used to discover common genetic components that span multiple individual genes. Individual genes or gene sequences may be considered as symbols that are part of the genome.

By comparing the relationships of the genes in different genomes it may be possible to construct components that include multiple genomes and genes, and accordingly evaluate a component's dependence on another components based on their presence or absence in a genome. This analysis can be performed over a population of individual organisms (multiple genomes) to analyze variance over individuals, or over a collection of different species, for example as an approach to identifying genetic bases for phenotypic differences.

For example, a method of detecting genetic relationships may comprise: interrogating, with at least one processor, each of a plurality of genomes for identifiable genes in each of the genomes; identifying dependencies between the identifiable genes based on the presence or absence of two or more identifiable genes in at least two of the plurality of genomes; constructing a plurality of component groups that include genomes that share identical genes; and constructing hierarchical relationships between the plurality of component groups based on the identified dependencies between the identifiable genes in the plurality of genomes, wherein the hierarchical relationships between the plurality of component groups indicate a dependency between a first component group and a second component group.

Data Storage Compression

Figure 8:
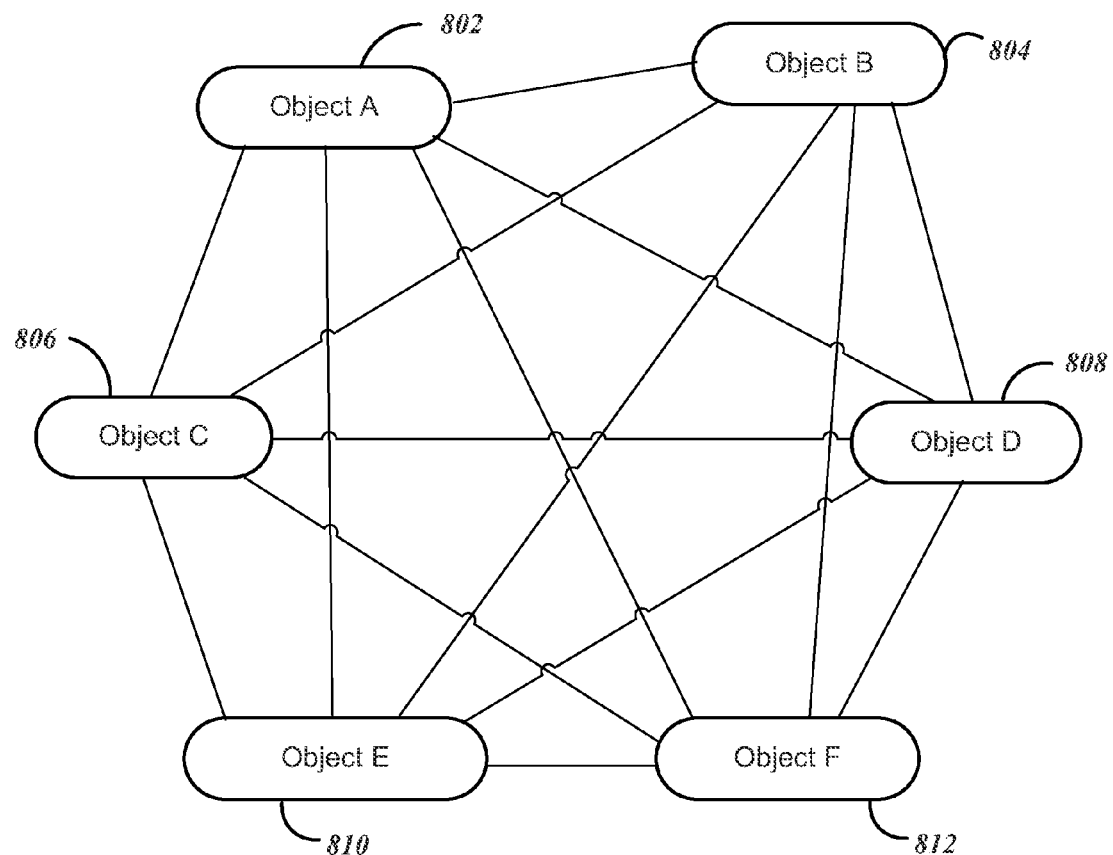
FIG. 8 illustrates an example of a set of objects with no unique symbols.

Referring to FIG. 8, objects that include each logical component may be grouped together based on their shared components. For example, collection 800 includes six different objects (802-812) that all include the same components and no unique symbols.

Generally, any collection of data where the order of the data in the collection is not required, such as a set, as opposed to a string, may be analyzed or compressed with embodiments of the procedures discussed herein. In the context of database design, example systems or methods can be used to construct a space-optimal representation of a collection of sets, since component items that appear in multiple sets needs to only be stored once after a graph of the collection of sets is constructed.

If the order that the components are stored in an object is not important or necessary to the object, the storage space allocated to common components to would be repeated in multiple objects may be compressed into a single instance for the entire set of objects.

For example, a method of computer program compression may comprise: interrogating each of a plurality of computer program objects for symbols that are embedded in the objects: identifying common the symbols in at least two of the plurality of computer program objects; constructing a plurality of component groups that include computer program objects that share identical symbols; identifying dependencies between the plurality of component groups; constructing hierarchical relationships between the plurality of component groups based on the identified dependencies; and eliminating storage of redundant sets of the common identifiable symbols in the plurality of component groups.

In another example, the computer program object may be reconstructed by extracting the computer program's objects and symbols from a graph based on the plurality of component groups and the hierarchical relationships.

Figure 9:
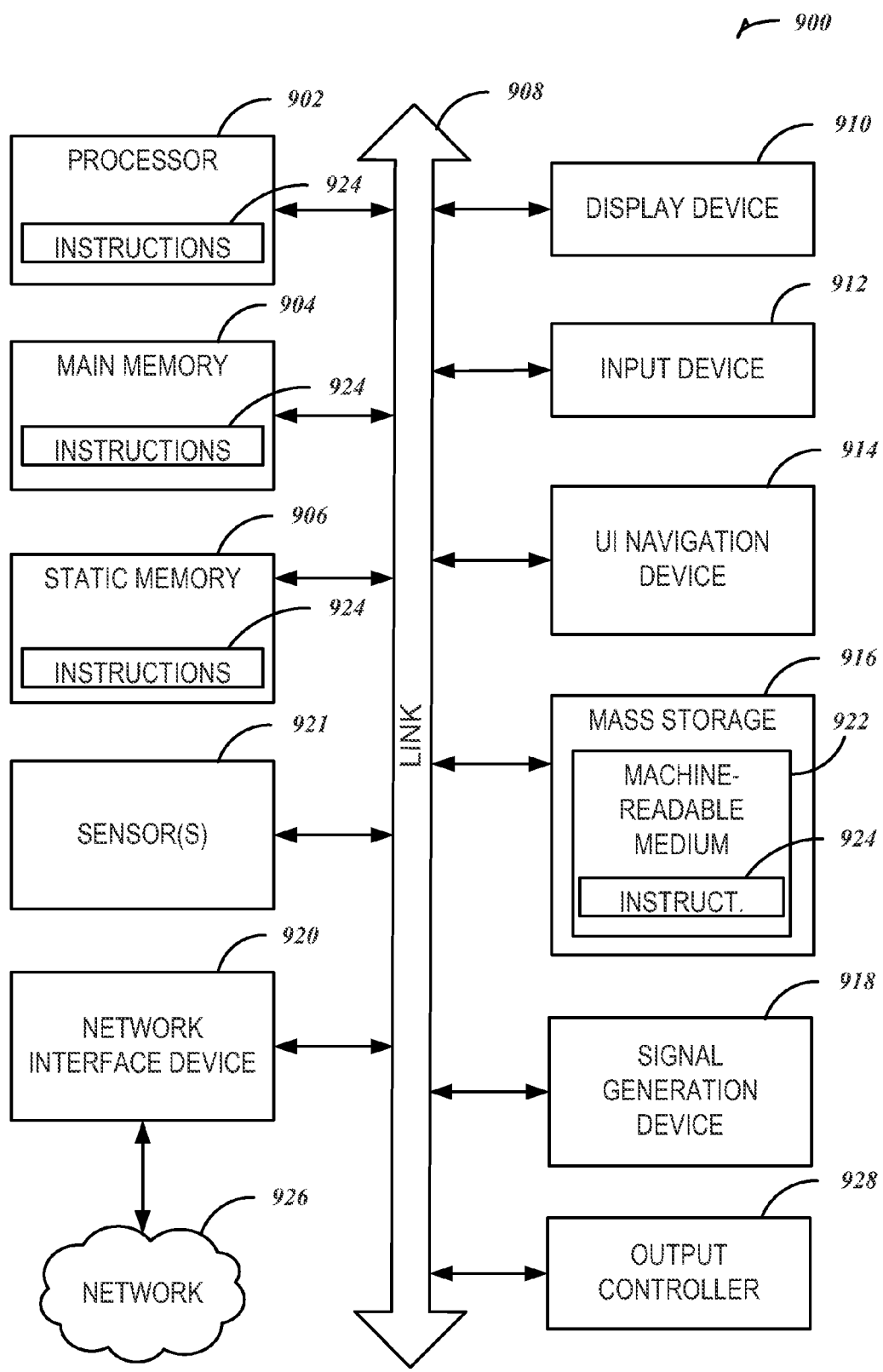
FIG. 9 illustrates a block diagram of an example machine upon which any one or more of the techniques discussed herein may be performed.

FIG. 9 illustrates a block diagram of an example machine 900 upon which any one or more of the techniques (e.g., methodologies) discussed herein may be performed. In alternative embodiments, the machine 900 may operate as a standalone device or may be connected (e.g., networked) to other machines. In a networked deployment, the machine 900 may operate in the capacity of a server machine, a client machine, or both in server-client network environments. In an example, the machine 900 may act as a peer machine in peer-to-peer (P2P) (or other distributed) network environment. The machine 900 may be a personal computer (PC), a tablet PC, a Personal Digital Assistant (PDA), a mobile telephone, a web appliance, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, logic or a number of components, modules, or mechanisms. Modules are tangible entities capable of performing specified operations and may be configured or arranged in a certain manner. In an example, circuits may be arranged (e.g., internally or with respect to external entities such as other circuits) in a specified manner as a module. In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside (1) on a non-transitory machine-readable medium or (2) in a transmission signal. In an example, the software, when executed by the underlying hardware of the module, causes the hardware to perform the specified operations.

Accordingly, the term "module" is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, each of the modules need not be instantiated at any one moment in time. For example, where the modules comprise a general-purpose hardware processor configured using software, the general-purpose hardware processor may be configured as respective different modules at different times. Software may accordingly configure a hardware processor, for example, to constitute a particular module at one instance of time and to constitute a different module at a different instance of time.

Machine (e.g., computer system) 900 may include a hardware processor 902 (e.g., a processing unit, a graphics processing unit (GPU), a hardware processor core, or any combination thereof), a main memory 904, and a static memory 906, some or all of which may communicate with each other via a link 908 (e.g., a bus, link, interconnect, or the like). The machine 900 may further include a display device 910, an input device 912 (e.g., a keyboard), and a user interface (UI) navigation device 914 (e.g., a mouse). In an example, the display device 910, input device 912, and UI navigation device 914 may be a touch screen display. The machine 900 may additionally include a mass storage (e.g., drive unit) 916, a signal generation device 918 (e.g., a speaker), a network interface device 920, and one or more sensors 921, such as a global positioning system (GPS) sensor, camera, video recorder, compass, accelerometer, or other sensor. The machine 900 may include an output controller 928, such as a serial (e.g., universal serial bus (USB), parallel, or other wired or wireless (e.g., infrared (IR)) connection to communicate or control one or more peripheral devices (e.g., a printer, card reader, etc.).

The mass storage 916 may include a machine-readable medium 922 on which is stored one or more sets of data structures or instructions 924 (e.g., software) embodying or utilized by any one or more of the techniques or functions described herein. The instructions 924 may also reside, completely or at least partially, within the main memory 904, within static memory 906, or within the hardware processor 902 during execution thereof by the machine 900. In an example, one or any combination of the hardware processor 902, the main memory 904, the static memory 906, or the mass storage 916 may constitute machine readable media.

While the machine-readable medium 922 is illustrated as a single medium, the term "machine readable medium" may include a single medium or multiple media (e.g., a centralized or distributed database, and/or associated caches and servers) that configured to store the one or more instructions 924.

The term "machine-readable medium" may include any tangible medium that is capable of storing, encoding, or carrying instructions for execution by the machine 900 and that cause the machine 900 to perform any one or more of the techniques of the present disclosure, or that is capable of storing, encoding or carrying data structures used by or associated with such instructions. Non-limiting machine-readable medium examples may include solid-state memories, and optical and magnetic media. Specific examples of machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 924 may further be transmitted or received over a communications network 926 using a transmission medium via the network interface device 920 utilizing any one of a number of transfer protocols (e.g., frame relay, internet protocol (IP), transmission control protocol (TCP), user datagram protocol (UDP), hypertext transfer protocol (HTTP), etc.). The term "transmission medium" shall be taken to include any intangible medium that is capable of storing, encoding or carrying instructions for execution by the machine 900, and includes digital or analog communications signals or other intangible medium to facilitate communication of such software.

Embodiments may be implemented in one or a combination of hardware, firmware and software. Embodiments may also be implemented as instructions stored on a computer-readable storage device, which may be read and executed by at least one processor to perform the operations described herein. A computer-readable storage device may include any non-transitory mechanism for storing information in a form readable by a machine (e.g., a computer). For example, a computer-readable storage device may include read-only memory (ROM), random-access memory (RAM), magnetic disk storage media, optical storage media, flash-memory devices, and other storage devices and media.

The Abstract is provided to comply with 37 C.F.R. Section 1.72(b) requiring an abstract that will allow the reader to ascertain the nature and gist of the technical disclosure. It is submitted with the understanding that it will not be used to limit or interpret the scope or meaning of the claims. The following claims are hereby incorporated into the detailed description, with each claim standing on its own as a separate embodiment.

What is claimed is:

1. A method of executable computer program inspection, comprising:

interrogating simultaneously, with at least one processor, each of a plurality of executable computer program objects stored in a tangible computer readable medium for one or more symbols that are embedded in the objects;

identifying dependencies between the symbols based on the presence or absence of the symbols in at least two of the plurality of executable computer program objects;

constructing a plurality of component groups, wherein each group of the plurality of component groups include executable computer program objects that share identical symbols, wherein the symbols of each component group are unique to that component group;

constructing a directed graph representation of hierarchical relationships between the plurality of component groups based on the identified dependencies between the symbols in the plurality of executable computer program objects, wherein the directed graph includes each component group of the plurality of component groups as a node of the directed graph and a directed edge from a first node of the directed graph to a second node of the directed graph if all the symbols of the component associated with the second node are also present in the component associated with the first node;

eliminating a component of the plurality of components that comprises exactly the same symbols as another component of the plurality of components; and storing the hierarchical relationships in a data structure.

2. The method of claim 1, wherein the hierarchical relationships between the plurality of component groups indicate a dependency between a first component group and a second component group.

3. The method of claim 2, comprising:

identifying component groups that are common to a set of executable computer program objects in the plurality of executable computer program objects.

4. The method of claim 3, comprising:

comparing the component groups against a database of known malware components.

5. The method of claim 2, comprising:

identifying component groups that are unique to a executable computer program object in the plurality of executable computer program objects.

6. The method of claim 1, comprising:

receiving the plurality of executable computer program objects.

7. The method of claim 6, wherein the plurality of executable computer program objects includes a plurality of executable computer programs.

8. The method of claim 1, comprising:

displaying the graphical representation.

9. The method of claim 1, comprising:

computing a hash value for each of the identifiable symbols;

wherein identical symbols are determined by comparing the hash value for each symbol.

10. A method of detecting genetic relationships, comprising:

interrogating simultaneously, with at least one processor, each of a plurality of genomes for identifiable genes in each of the genomes;

identifying dependencies between the identifiable genes based on the presence or absence of two or more identifiable genes in at least two of the plurality of genomes;

constructing a plurality of component groups, wherein each group of the plurality of component groups includes genomes that share identical genes, wherein the genes of each component group are unique to that component group;

constructing a directed graph representation of hierarchical relationships between the plurality of component groups based on the identified dependencies between the identifiable genes in the plurality of genomes, wherein the hierarchical relationships between the plurality of component groups indicate a dependency between a first component group and a second component group, wherein the directed graph includes each component group of the plurality of component groups as a node of the directed graph and a directed edge from a first node of the directed graph to a second node of the directed graph if all the genes of the component associated with the second node are also present in the component associated with the first node;

eliminating a component group of the plurality of component groups that comprises exactly the same symbols as another component group of the plurality of component groups; and generating a report that details the hierarchical relationships between the plurality of component groups.

11. The method of claim 10, comprising:
identifying component groups that are common to a set of genomes in the plurality of genomes.

12. The method of claim 10, comprising:
identifying component groups that are unique to a genomes in the plurality of genomes.

13. The method of claim 10, comprising:
displaying the graphical representation.

14. A method of compressing a computer program stored on a machine-readable medium, comprising:
interrogating simultaneously, with at least one processor, each of a plurality of executable computer program objects for symbols that are embedded in the objects on the machine-readable medium;
identifying common symbols in at least two of the plurality of computer program objects;
constructing a plurality of component groups, wherein each component group of the plurality of component groups includes executable computer program objects that share identical symbols, wherein the symbols of each component group are unique to that component group;
identifying dependencies between the plurality of component groups;
constructing a directed graph representation of hierarchical relationships between the plurality of component groups based on the identified dependencies, wherein the directed graph includes each component group of the plurality of component groups as a node of the directed graph and a directed edge from a first node of the directed graph to a second node of the directed graph if all the symbols of the component associated with the second node are also present in the component associated with the first node; and
eliminating storage of redundant sets of the common identifiable symbols in the plurality of component groups on the machine-readable medium.

15. The method of claim 14 comprising:
extracting one of the plurality of executable computer program objects and symbols that are embedded in the one executable computer program object based on the plurality of component groups and the hierarchical relationships.

16. At least one machine-readable medium comprising a plurality of instructions that in response to being executed on a computing device, cause the computing device to:
interrogate simultaneously each of a plurality of executable objects stored on a machine-readable medium for one or more symbols that are embedded in the executable objects;
identify dependencies between the symbols based on the presence or absence of the symbols in at least two of the plurality of executable objects;
construct a plurality of component groups, wherein each component group of the plurality of component groups includes executable objects that share identical symbols, wherein the symbols of each component group are unique to that component group; and
construct a directed graph representation of hierarchical relationships between the plurality of component groups based on the identified dependencies between the symbols in the plurality of executable objects, wherein the directed graph includes each component group of the plurality of component groups as a node of the directed graph and a directed edge from a first node of the directed graph to a second node of the directed graph if all the symbols of the component associated with the second node are also present in the component associated with the first node.

17. At least one non-transitory machine-readable medium comprising a plurality of instructions that in response to being executed on a computing device, cause the computing device to:
access a plurality of executable computer program objects;
interrogate simultaneously each of a plurality of executable computer program objects stored for one or more symbols that are embedded in the objects;
identify dependencies between the symbols based on the presence of the symbols in at least two of the plurality of executable computer program objects;
construct a plurality of component groups, wherein each component group of the plurality of component groups includes executable computer program objects that share identical symbols, wherein the symbols of each component group are unique to that component group; and
construct a directed graph representation of hierarchical relationships between the plurality of component groups based on the identified dependencies between the symbols in the plurality of executable computer program objects, wherein the directed graph includes each component group of the plurality of component groups as a node of the directed graph and a directed edge from a first node of the directed graph to a second node of the directed graph if all the symbols of the component associated with the second node are also present in the component associated with the first node.

18. The at least one non-transitory machine-readable medium of claim 17, comprising instructions to:
identify component groups that are common to a set of executable computer program objects in the plurality of computer program objects.

19. The at least one non-transitory machine-readable medium of claim 17, comprising instructions to:
identify component groups that are unique to a executable computer program object in the plurality of computer program objects.

20. An object inspection system comprising:
a storage element to store a plurality of executable computer program objects;

one or more processors coupled to the storage element configured to interrogate simultaneously the plurality of executable computer program objects for one or more symbols that are embedded in the executable computer program objects, and to generate an object-identifier associated with each one of the interrogated executable computer program objects and a symbol-identifier for each symbol in the interrogated executable computer program objects;

an analysis module configured to: identify dependencies between the symbols based on the presence or absence of the symbols in at least two of the plurality of executable computer program objects, construct a plurality of component groups, wherein each component group of the plurality of component groups includes executable computer program objects that share identical symbols, and construct hierarchical relationships between the plurality of component groups based on the identified dependencies between the symbols in the plurality of executable computer program objects, and store the hierarchical relationships in a data structure, wherein the symbols of each component group are unique to that component group; and an output module configured to generate a report that details the hierarchical relationships between the plurality of component groups stored in the data structure, wherein the report includes a directed graph representation of the hierarchical relationships, wherein the directed graph includes each component group of the plurality of component groups as a node of the directed graph and a directed edge from a first node of the directed graph to a second node of the directed graph if all the symbols of the component associated with the second node are also present in the component associated with the first node.

21. The system of claim 20, wherein the hierarchical relationships between the plurality of component groups indicate a dependency between a first component group and a second component group.

\* \* \* \* \*